(12) United States Patent
Trussardi

(10) Patent No.: US 9,481,650 B2
(45) Date of Patent: Nov. 1, 2016

(54) PROCESS FOR THE PREPARATION OF 2-TRIFLUOROMETHYL ISONICOTINIC ACID AND ESTERS

(71) Applicant: Hoffmann-La Roche Inc., Little Falls, NJ (US)

(72) Inventor: René Trussardi, Birsfelden (CH)

(73) Assignee: Hoffmann La Roche Inc., Little Falls, NJ (US)

( * ) Notice: Subject to any disclaimer, the term of this patent is extended or adjusted under 35 U.S.C. 154(b) by 0 days.

(21) Appl. No.: 14/442,971

(22) PCT Filed: Nov. 13, 2013

(86) PCT No.: PCT/EP2013/073715
§ 371 (c)(1),
(2) Date: May 14, 2015

(87) PCT Pub. No.: WO2014/076127
PCT Pub. Date: May 22, 2014

(65) Prior Publication Data
US 2015/0291530 A1    Oct. 15, 2015

(30) Foreign Application Priority Data
Nov. 16, 2012 (EP) .................................... 12193065

(51) Int. Cl.
*C07D 213/79* (2006.01)
*C07D 213/81* (2006.01)
*C07D 213/84* (2006.01)

(52) U.S. Cl.
CPC ............ *C07D 213/84* (2013.01); *C07D 213/79* (2013.01); *C07D 213/81* (2013.01)

(58) Field of Classification Search
None
See application file for complete search history.

(56) References Cited

FOREIGN PATENT DOCUMENTS

| EP | 1348706 A1 | 10/2003 |
|----|------------|---------|
| EP | 1790650 A1 | 5/2007 |
| WO | 2010/100050 A1 | 9/2010 |
| WO | 2011/060389 A1 | 5/2011 |
| WO | 2012/068450 A1 | 5/2012 |

OTHER PUBLICATIONS

Gong et al, Chinese Journal of Chemistry (2001), 19(12), 1263-1267.*
Albanese-Walker et al., "Improved Carbonylation of Heterocyclic Chlorides and Electronically Challenging Aryl Bromides" Org. Lett. 6(13):2097-2100 ( 2004).
Barnard, "Palladium-Catalyzed CarbonylationsA Reaction Come of Age" Organometallics 27(21):5402-5422 ( 2008).
International Search Report issued in International Application No. PCT/EP2013/073715, mailed Dec. 19, 2013 (in 6 pages).
Liu et al., "Radiosynthesis and Bioimaging of the Tuberculosis Chemotherapeutics Isoniazid, Rifampicin and Pyrazinamide in Baboons" J. Med. Chem. 53:2882-2891 ( 2010).
Schlosser et al., "The Direct Metalization and Subsequent Functionalization of Trifluoromethyl-Substituted Pyridines and Quinolines" Eur. J. Org. Chem.:1569-1575 ( 2003).

* cited by examiner

*Primary Examiner* — Zinna Northington Davis

(57) ABSTRACT

The invention relates to a novel process for the preparation of 2-trifluoromethyl isonicotinic acid and esters of the formula I which involves a palladium catalyzed carbonylation or cyanation step wherein $R^1$ is hydrogen or $Q_{1-6}$-alkyl. The 2-trifluoromethyl isonicotinic acid and esters of the formula I are versatile intermediates for the preparation of active pharmaceutical and agrochemical agents such as for instance TAAR 1 agonists of the formula III.

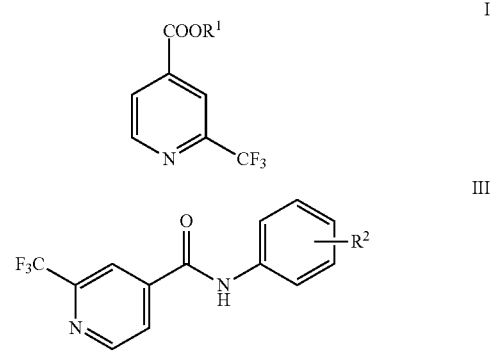

22 Claims, No Drawings

PROCESS FOR THE PREPARATION OF 2-TRIFLUOROMETHYL ISONICOTINIC ACID AND ESTERS

CROSS-REFERENCE TO RELATED APPLICATIONS

This application is a 371 application of International Application No. PCT/EP2013/073715, filed on Nov. 13, 2013, which claims priority to European Patent Application No. 12193065.5, filed on Nov. 16, 2012, the entire contents of which are incorporated herein by reference.

The invention relates to a novel process for the preparation of 2-trifluoromethyl isonicotinic acid and esters of the formula

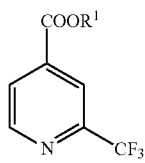

wherein $R^1$ is hydrogen or $C_{1-6}$-alkyl.

The 2-trifluoromethyl isonicotinic acid and esters of the formula I are versatile intermediates for the preparation of active pharmaceutical and agrochemical agents (e.g. Manfred Schlosser et al., Eur. J. Org. Chem. 2003, 1559-1568).

The invention further relates to the use of the process of the present invention for a process for the preparation of TAAR1 agonists of the formula

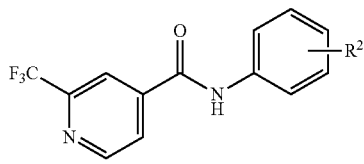

wherein
$R^2$ is $(CH_2)_n$—$(O)_o$-heterocycloalkyl, optionally substituted by $C_{1-6}$-alkyl, hydroxy, halogen, or by —$(CH_2)_p$-aryl;
n is 0, 1, 2;
o is 0, 1;
p is 0, 1, 2;
or a pharmaceutically suitable acid addition salt thereof.

TAAR agonists of the formula III have been disclosed in PCT Publ. WO 2012/016879.

Various syntheses are described in the art.

Chikara Fukaya et al., Chem. Pharm. Bull. 38(9) 2446-2458 (1990) for instance suggest to first methylate 4-chloro-2-trifluoromethylpyridine with trimethylaluminium and to subsequently oxidize the methyl group with $KMnO_4$. The resulting yield is low and the process is not applicable on technical scale.

Manfred Schlosser et al., Eur. J. Org. Chem. 2003, 1559-1568) describe the preparation of 2-trifluoromethyl-4-pyridine carboxylic acid in an overall yield of 45% from 2-trifluoro pyridine by initial deprotonation, subsequent iodination at the 3-position, followed by halogen migration and final carboxylation. Also this synthesis is not applicable on technical scale.

Manfred Schlosser et al., Eur. J. Org. Chem. 2003, 1569-1575 describe a synthesis which starts start from 2-trifluoromethylpyridine which is treated with the amide base LITMP (Li-2,2,5,5-tetramethylpiperidine) at minus 70° C. followed by a treatment with carbon dioxide. This synthesis shows low selectivity towards the desired 2-trifluoromethyl isonicotinic acid, applies an expensive amide base and is as well difficult to handle on technical scale.

The object of the present invention therefore was to find a process which is able to overcome the drawbacks known from the processes known in the art and which is able to be performed on technical scale.

It was found that the object could be reached with the process as outlined below.

The process for the preparation of 2-trifluoromethyl isonicotinic acid and esters of the formula

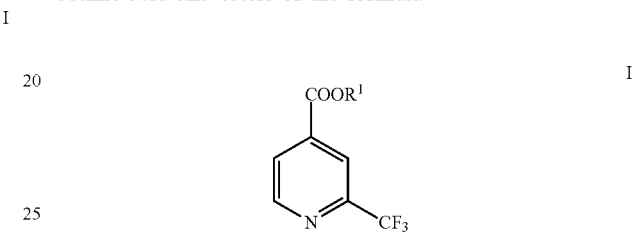

wherein $R^1$ is hydrogen or $C_{1-6}$-alkyl, comprises the conversion of a 2-trifluoromethyl pyridine derivative of the formula

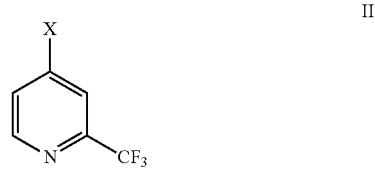

wherein X is halogen or —$OSO_2CY_3$, wherein Y is halogen, in the presence of a palladium complex catalyst.

The following definitions are set forth to illustrate and define the meaning and scope of the various terms used to describe the invention herein.

The term "$C_{1-6}$-alkyl" relates to a branched or straight-chain monovalent saturated aliphatic hydrocarbon radical of one to six carbon atoms, preferably one to four, more preferably one to two carbon atoms. This term is further exemplified by radicals as methyl, ethyl, n-propyl, i-propyl, n-butyl, s-butyl or t-butyl, pentyl and its isomers and hexyl and its isomers.

The term "halogen" refers to fluorine, chlorine, bromine or iodine, but particularly to chlorine.

The term "aryl", relates to an aromatic carbon ring such as to the phenyl or naphthyl ring, preferably the phenyl ring.

The term "heterocycloalkyl" refers to a non-aromatic 5 to 6 membered monocyclic ring which can comprise 1, 2 or 3 heteroatoms selected from nitrogen, oxygen and/or sulphur, such as piperazinyl, piperidinyl, morpholinyl, pyrrolidinyl or thiomorpholinyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The 2-trifluoromethyl pyridine derivatives of the formula II are commercially available. They can alternatively be synthesized according to the teaching of the PCT Int. Publication WO 2011/161612 or the literature cited therein.

Suitable 2-trifluoromethyl pyridine derivatives of the formula II are those, wherein X is fluorine, chlorine, bromine, iodine or trifluoromethanesulfonyl. 4-chloro-2-trifluoro pyridine (X=chlorine) is particularly used.

Suitable palladium complex catalysts are either commercially available or can be prepared in situ following methods known to the skilled in the art.

They can be selected from Bis(benzonitrile)palladium(II)-chloride (CAS No. 14220-64-5), Tris(dibenzylideneacetone)dipalladium(0) (CAS: 51364-51-3), (Palladium(II)acetate (CAS No. 3375-31-3) or Palladium(II)chloride CAS No. 7647-10-1 with the ligands selected from 1,1-Bis(diphenylphosphino)ethane (dppe), 1,1'-Bis(diphenylphosphino)ferrocene (dppf), Bis(diphenylphosphino)methane (dppm), 1,3-Bis(diphenylphosphino)propane (dppp), 4,5-Bis(diphenylphosphino) 9,9-dimethylxanthene or from triphenylphosphane.

In one embodiment the conversion comprises the reaction of the 2-trifluoromethyl pyridine derivative of the formula II with carbon monoxide (CO) in the presence of the reactant $R^1OH$, wherein $R^1$ is as above.

Particularly selected palladium complex catalysts for this conversion is Palladium(II)chloride with the ligands 1,1'-Bis(diphenylphosphino)ferrocen (dppf) or 1,3-Bis(diphenylphosphino)propane (dppp) preferably in their commercially available form 1,1'-Bis(diphenylphosphino)ferrocene-palladium(II)dichloride dichloromethane adduct (CAS No. 95464-05-4) and (1,3-Bis(diphenylphosphino)propane)-palladium(II)chloride (CAS No. 59831-02-6).

The conversion can be performed under a CO pressure of 5 bar to 100 bar, more particularly of 60 bar to 70 bar.

The reaction temperature is as a rule selected between 50° C. and 170° C., particularly between 120° C. and 140° C.

Advantageously a base is present which can either be selected from an organic base, like a tertiary amine or from an inorganic base, like an alkali hydrogen carbonate or an alkali phosphate. A suitable representative for an organic base is a tri-alkylamine, like triethylamine and suitable representatives for inorganic bases are for instance sodium hydrogen carbonate or tri-potassium phosphate.

The reactant $R^1OH$ is either water ($R^1$=H) affording the 2-trifluoromethyl isonicotinic acid or a $C_{1-6}$-alcohol ($R^1$=$C_{1-6}$-alkyl) affording the respective 2-trifluoromethyl isonicotinic acid esters.

Particularly $C_{1-4}$-alcohols such as methanol, ethanol, n-propanol, i-propanol, n-butanol, s-butanol or t-butanol, more particularly methanol, ethanol, or i-propanol and even more particularly methanol are used.

In case of the conversion with water an organic solvent selected from ethers like dioxane or tetrahydrofuran or lower alcohols like methanol, ethanol or i-propanol can be added. Tetrahydrofuran was found to be particularly suitable.

In the case of the conversion with a $C_{1-6}$-alcohol the initial conversion with carbon monoxide can be followed by a treatment with a hydrogen chloride producing agent to foster complete ester formation.

Suitable hydrogen chloride producing agents can be selected from inorganic acid chlorides, like hydrogen chloride or from organic acid chlorides such as thionyl chloride or acetylchloride. Thionyl chloride was found to be most suitable.

The treatment with the hydrogen producing agent is usually performed at reflux conditions of the reaction mixture.

In a further embodiment the conversion comprises the reaction of the 2-trifluoromethyl pyridine derivative of the formula I with a metal cyanide MCN, wherein M stands for a metal ion to form a nitrile of formula IV

V and the further hydrolysis or esterification to form the 2-trifluoromethyl isonicotinic acid and esters of the formula I.

The palladium complex catalyst selected for this conversion as a rule is Pd(PPh$_3$)$_4$(0), 1,1'-Bis(diphenylphosphino)ferrocene-palladium(II)dichloride dichloromethane adduct (CAS No. 95464-05-4), Pd(P-tert.-Bu$_3$)$_2$, Tris(dibenzylideneacetone)dipalladium(0) or Pd(TFA)$_2$ with the ligands 1,1'-Bis(diphenylphosphino)ferrocen (dppf) or rac-2-(di-tert.-butylphosphino)-1,1-binaphthyl.

Suitable metal cyanides MCN are zinc cyanide, or zinc cyanide with a mixture with sodium cyanide or potassium cyanide, but particularly is zinc cyanide.

The reaction temperature is usually selected between 50° C. and 120° C.

The reaction takes place in a suitable organic solvent such as in N,N.dimethyl formamide, N,N-dimethyl acetamide, N-methyl-2-pyrrolidone, N-ethyl-2-pyrrolidone, but preferred in N,N-dimethyl formamide.

The nitrile of formula IV can be isolated from the reaction mixture for instance by way of extraction with a suitable solvent such as with tert. methyl butyl ether and evaporation of the solvent. Vacuum distillation of the crude nitrile can afford the nitrile in high purity.

The hydrolysis of the nitrile of formula IV to the 2-trifluoromethyl isonicotinic acid of formula I with $R^1$=hydrogen is performed with a suitable base which can be selected from an alkali hydroxide such as sodium-, potassium- or lithium hydroxide.

As a rule the reaction takes place in a suitable solvent such as in lower alcohols like methanol, ethanol, 1-propanol, 2-propanol at reflux conditions.

Isolation of the product can happen after acidification with aqueous hydrochloric acid by filtration.

The esterification of the nitrile of formula IV to the 2-trifluoromethyl isonicotinic acid ester of formula I with $R^1$=$C_{1-6}$-alkyl is performed with an alcohol $R^1OH$, wherein $R^1$ is $C_{1-6}$-alkyl in the presence of hydrogen chloride gas or a hydrogen chloride producing agent.

Particularly $C_{1-4}$-alcohols such as methanol, ethanol, n-propanol, i-propanol, n-butanol, s-butanol or t-butanol, more particularly methanol, ethanol, or i-propanol and even more particularly methanol are used.

Suitable hydrogen chloride producing agents can be selected from inorganic acid chlorides, like hydrogen chloride or from organic acid chlorides such as thionyl chloride or acetyl chloride. Acetyl chloride was found to be most suitable.

The reaction as a rule takes place under reflux conditions of the respective alcohol.

Isolation of the respective ester can happen by way of extraction with a suitable solvent such as with tert. methyl butyl ether out of the neutralized reaction mixture and by subsequent evaporation of the organic solvent.

The embodiment comprising the conversion of the 2-trifluoromethyl pyridine derivative of the formula II with carbon monoxide (CO) in the presence of the reactant $R^1OH$, wherein $R^1$ is as above is preferred.

As indicated above the invention further comprises the use of the process of the present invention in a process for the preparation of TAAR1 agonists of the formula

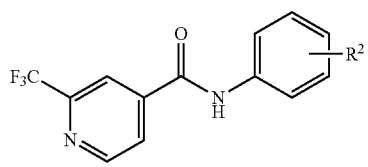

III wherein
$R^2$ is $(CH_2)_n$—$(O)_o$-heterocycloalkyl, optionally substituted by $C_{1-6}$-alkyl, hydroxy, halogen, or by —$(CH_2)_p$-aryl;
n is 0, 1, 2;
o is 0, 1;
p is 0, 1, 2;
or a pharmaceutically suitable acid addition salt thereof.

The compounds of formula III can for instance be prepared according to the PCT Publ. WO 2012/016879 by reacting the 2-trifluoromethyl isonicotinic acid and esters of the formula I with an optionally protected arylamine of formula IV

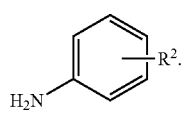

IV

Optionally protected in this context means that the nitrogen heteroatom of the heterocycloalkyl moiety $R^2$ is protected with a common amino protecting group such as for instance with Boc. In that case the process further comprises the removal of the amino protecting group for instance under acidic conditions.

EXAMPLES

Abbreviations:

| | |
|---|---|
| DMF | N,N'-dimethylformamide |
| MTBE | Methyl tert. butyl ether |
| PdCl₂(dppp) | dichloro(diphenylphosphine-propane)palladium(II) |
| r.t. | Room temperature |
| THF | tetrahydrofuran |

Example 1

Preparation of 4-Chloro-2-trifluoromethyl-pyridine

In a 25 ml round bottom flask equipped with a reflux condenser, magnetic stirrer and a inert gas supply 1.63 g (10.0 mmol) 4-Hydroxy-2-trifluoromethyl-pyridine was treated with 4.9 ml cyclohexane and 0.077 ml DMF, at room temperature 2.19 ml (25.0 mmol) oxalyl chloride was added, the mixture was heated to reflux for 3 hours, cooled to room temperature, slowly (gas evolution) 18 ml water was added dropwise, the mixture was extracted with 18 ml MTBE, the separated organic layer was washed with 1M NaHCO₃ and the separated organic layer was dried with anhydrous Na₂SO₄, filtered and evaporated at reduced pressure, the crude black liquid was treated with 12 ml n-hexane, stirred for 5 min at rt, filtered and evaporated under reduced pressure to obtain 0.9 g 4-Chloro-2-trifluoromethyl pyridine as yellow liquid.

GC-EI-MS: M 181⁻/M 183⁺.

Example 2

Preparation of 2-Trifluoromethyl-isonicotinic acid methyl ester from 4-Chloro-2-trifluoromethylpyridine A mixture of 76.8 g (423 mmol) 4-Chloro-2-trifluoromethyl-pyridine, 7.67 g (7.67 mmol) 1,1'-Bis(diphenylphosphino)ferrocene-palladium(II)dichloride dichloromethane adduct and 88.4 ml (635 mmol) triethylamine in 792 ml methanol was stirred under 70 bar CO for 18 hour at 130° C. The crude mixture (contain ~30% acid), was concentrated under reduced pressure to a ~20% mixture, treated slowly with 30.9 ml (423 mmol) thionyl chloride and refluxed for one hour. The mixture was evaporated under reduced pressure, the residue was treated with 450 ml water and 450 ml MTBE, and the formed suspension was filtered. From the filtrate, the organic layer was separated and extracted with 225 ml 1M NaHCO₃, the separated organic layer was dried with anhydrous Na₂SO₄, filtered and evaporated under reduced pressure to obtain crude 2-trifluoromethyl-isonicotinic acid methyl ester which was distilled at ~20 mmbar/bp 97-99° C., to obtain 80.7 g 2-trifluoromethyl-isonicotinic acid methyl ester as colorless liquid.

GC-EI-MS: M 205⁺.

Example 3

Preparation of 2-Trifluoromethyl-isonicotinic acid ethyl ester from 4-Chloro-2-trifluoromethyl pyridine A mixture of 182 mg (1.0 mmol) 4-Chloro-2-trifluoromethyl pyridine, 18.2 mg (0.022 mmol) 1,1'-Bis(diphenylphosphino)ferrocene-palladium(II)dichloride dichloromethane adduct and 0.21 ml (1.50 mmol) triethylamine in 3.0 ml ethanol was stirred under 70 bar CO for 18 hour at 130° C., the crude mixture was evaporated under reduced pressure, the residue was treated with 4.0 ml 0.5M HCl and 4.0 ml MTBE, the formed suspension was filtered, the organic layer was separated and extracted with 2.0 ml 1M NaHCO₃, the separated organic layer was dried with anhydrous Na₂SO₄, filtered and evaporated under reduced pressure to obtain crude 2-trifluoromethyl-isonicotinic acid ethyl ester which was stirred with 2.0 ml cyclohexane for 10 min at room temperature, the light cloudy brown solution was filtered and the filtrate was evaporated under reduced pressure to obtain 113 mg 2-trifluoromethyl-isonicotinic acid ethyl ester as light brown liquid.

GC-EI-MS: M 219⁺.

Example 4

Preparation of 2-Trifluoromethyl-isonicotinic acid isopropyl ester from 4-Chloro-2-trifluoromethyl pyridine A mixture of 182 mg (1.0 mmol) 4-Chloro-2-trifluoromethyl pyridine, 18.2 mg (0.022 mmol) 1,1'-Bis(diphenylphosphino)ferrocene-palladium(II)dichloride dichloromethane adduct and 0.21 ml (1.5 mmol) triethylamine in 3.0 ml 2-propanol was stirred under 70 bar CO for 18 hour at 130° C., the crude mixture was evaporated under reduced pressure, the residue was treated with 4.0 ml 0.5M HCl and 4.0 ml MTBE, the formed suspension was filtered, the organic layer was separated and extracted with 2.0 ml 1M $NaHCO_3$, the separated organic layer was dried with anhydrous $Na_2SO_4$, filtered and evaporated under reduced pressure to obtain crude 2-trifluoromethyl-isonicotinic acid ethyl ester which was stirred with 2.0 ml cyclohexane for 10 min at room temperature, the light cloudy brown solution was filtered and the filtrate was evaporated under reduced pressure to obtain 134 mg 2-trifluoromethyl-isonicotinic acid isopropyl ester as light brown liquid.

GC-EI-MS: M $233^+$.

Example 5

Preparation of trifluoro-methanesulfonic acid 2-trifluoromethyl-pyridin-4-yl ester In a 25 ml round bottom flask equipped with a magnetic stirrer and a inert gas supply 1.63 g (10.0 mmol) 2-Trifluoromethyl-pyridin-4-ol was dissolved 8.15 ml dichloromethane, 2.04 ml (12.0 mmol) N-ethyldiisopropylamine was added and the solution was cooled to 0-5° C. and 1.86 ml (11.0 mmol) Trifluoromethanesulfonic anhydride was added dropwise, the mixture was stirred at 0-5° C. for 1 hour, the mixture was extracted with 10 ml 0.5M HCl, the separated organic layer was dried with anhydrous $Na_2SO_4$ and evaporated under reduced pressure. The residue was purified over 15 g silica with cyclohexane/MTBE to obtain 1.58 g trifluoro-methanesulfonic acid 2-trifluoromethyl-pyridin-4-yl ester as light yellow oil.

GC-EI-MS: M $295^+$.

Example 6

Preparation of 2-Trifluoromethyl-isonicotinic acid methyl ester from trifluoro-methanesulfonic acid 2-trifluoromethyl-pyridin-4-yl ester A mixture of 295 mg (1.0 mmol) trifluoro-methanesulfonic acid 2-trifluoromethyl-pyridin-4-yl ester 18.1 mg (0.022 mmol) 1,1'-Bis(diphenylphosphino)ferrocene-palladium(II) dichloride dichloromethane adduct and 0.21 ml (1.5 mmol) triethylamine in 4.0 ml methanol was stirred under 70 bar CO for 18 hour at 130° C., the crude mixture (contain ~30% acid) was treated with 0.073 ml (1.0 mmol) thionyl chloride refluxed for one hour, the mixture was evaporated under reduced pressure, the residue was treated with 4.0 ml water and 4.0 ml MTBE, the formed suspension was filtered the separated organic layer was extracted with 4.0 ml 1M $NaHCO_3$, the separated organic layer was dried with anhydrous $Na_2SO_4$, filtered and evaporated under reduced pressure to obtain crude 2-trifluoromethyl-isonicotinic acid methyl ester which was treated with 2.0 ml cyclohexane, the mixture was filtered and evaporated under reduced pressure to obtain 136 mg 2-trifluoromethyl-isonicotinic acid methyl ester as light yellow liquid.

GC-EI-MS: M $205^+$.

Example 7

Preparation of 2-Trifluoromethyl-isonicotinic acid methyl ester from 4-Bromo-2-trifluoromethyl pyridine hydrobromide A mixture of 307 mg (1.0 mmol) 4-Bromo-2-trifluoromethyl pyridine hydrobromide, 18.1 mg (0.022 mmol) 1,1'-Bis(diphenylphosphino)ferrocene-palladium(II)dichloride dichloromethane adduct and 0.35 ml (2.5 mmol) triethylamine in 4.0 ml methanol was stirred under 70 bar CO for 18 hour at 130° C., the crude mixture (contain ~30% acid) was treated with 0.073 ml (1.0 mmol) thionyl chloride refluxed for one hour, the mixture was evaporated under reduced pressure, the residue was treated with 4.0 ml water and 4.0 ml MTBE, the formed suspension was filtered, the separated organic layer was extracted with 2.0 ml 1M $NaHCO_3$, the separated organic layer was dried with anhydrous $Na_2SO_4$, filtered and evaporated under reduced pressure to obtain crude 2-trifluoromethyl-isonicotinic acid methyl ester which was stirred with 2.0 ml cyclohexane for 15 min, filtered and evaporated under reduced pressure to obtain 112 mg 2-trifluoromethyl-isonicotinic acid methyl ester as colorless liquid.

GC-EI-MS: M $205^+$.

Example 8

Preparation of 2-Trifluoromethyl-isonicotinic acid methyl ester from 4-Iodo-2-trifluoromethyl pyridine A mixture of 165 mg (0.60 mmol) 4-Iodo-2-trifluoromethyl pyridine, 16.5 mg (0.020 mmol) 1,1'-Bis(diphenylphosphino)ferrocene-palladium(II)dichloride dichloromethane adduct and 0.126 ml (0.907 mmol) triethylamine in 3.0 ml methanol was stirred under 70 bar CO for 18 hour at 130° C., the crude mixture was treated with 0.044 ml (1.0 mmol) thionyl chloride and refluxed for one hour, evaporated under reduced pressure, the residue was treated with 2.0 ml water and 2.0 ml MTBE, the formed suspension was filtered, the organic layer was separated and extracted with 2.0 ml 1M $NaHCO_3$, the separated organic layer was dried with anhydrous $Na_2SO_4$, filtered and evaporated under reduced pressure to obtain crude 2-trifluoromethyl-isonicotinic acid ethyl ester which was stirred with 2.0 ml cyclohexane for 10 min at room temperature, the light brown suspension was filtered and the filtrate was evaporated under reduced pressure to obtain 104 mg 2-trifluoromethyl-isonicotinic acid methyl ester as light brown liquid. GC-EI-MS: M $205^+$.

Example 9

Preparation of 2-Trifluoromethyl-isonicotinic acid from 4-Chloro-2-trifluoromethyl pyridine A mixture of 182 mg (1.0 mmol) 4-Chloro-2-trifluoromethyl pyridine, 18.0 mg $PdCl_2(dppp)$ and 210 mg sodium hydrogencarbonate in 1.5 ml THF and 1.5 ml water was stirred under 70 bar CO for 20 hour at 120° C., THF was removed under reduced pressure, 0.5 ml 2M NaOH was added and the suspension was filtered. The clear solution was treated with 0.52 ml hydrochloric acid 25%, stirred for 1 h at rt, filtered and the white crystals were dried at 40° C., to obtain 146 mg 2-trifluoromethyl-isonicotinic acid. GC-EI-MS: M 191+.

Example 10

Preparation of 2-(Trifluoromethyl)pyridine-4-carbonitrile from 4-Choro-2-trifluoromethyl pyridine A mixture of 4.0 g (22.0 mmol) 4-Chloro-2-trifluoromethyl pyridine in 40.0 ml DMF was flushed with argon, 0.98 g (1.76 mmol) 1,1'-Bis(diphenylphosphino)ferrocene (CAS: 12150-46-8), 1.01 g (1.10 mmol) Tris(dibenzylideneacetone)dipalladium(0) (CAS: 51364-51-3) and 2.59 g (22.0 mmol) zinc cyanide was added. The mixture was flushed with argon and stirred for 15 hour at 85-90° C., the black mixture was cooled to 5-10° C., 110 ml water and 110 ml MTBE was added, stirred for a half hour at r.t. then filtered over a glass fibre filter, the filter cake was washed with 15 ml MTBE, the organic layer from the filtrate was separated, and washed twice with 110 ml water, the separated organic layer was dried with anhydrous $Na_2SO_4$, filtered and evaporated under reduced pressure to obtain crude 4.20 g 2-(trifluoromethyl)pyridine-4-carbonitrile which contain dibenzylideneacetone as impurity. The crude product was treated with 8.40 ml MTBE, and the formed suspension was stirred for 15 min at r.t., then filtered and the filter cake was washed with 4.0 ml MTBE. The brown filtrate was evaporated under reduced pressure to obtain 3.60 g of the title product as brown oil, which was distilled at 10 mbar/b.p. 58-60° C. to obtain 2.75 g 2-(trifluoromethyl)pyridine-4-carbonitrile as colorless liquide
GC-EI-MS: M 172+.

Example 11

Preparation of 2-Trifluoromethyl-isonicotinic acid from 2-(Trifluoromethyl)pyridine-4-carbonitrile A mixture of 172 mg (1.0 mmol) 2-(trifluoromethyl) pyridine-4-carbonitrile in 0.86 ml ethanol was treated with, 0.20 g (5.0 mmol) sodium hydroxide. The mixture was refluxed for 1.5 hours, cooled to r.t. and the yellow suspension was cooled to r.t., 3.0 ml water and 0.65 ml hydrochloric acid was added. The suspension was cooled to 0-5° C. form 30 min., filtered and washed with 2.0 ml water. The beige crystals were dried at 40° C./15 mbar/2 hour to obtain 0.15 g 2-trifluoromethyl-isonicotinic acid. GC-EI-MS: M 191+.

Example 12

Preparation of 2-Trifluoromethyl-isonicotinic acid methyl ester from 2-(Trifluoromethyl)pyridine-4-carbonitrile A mixture of 172 mg (1.0 mmol) 2-(trifluoromethyl) pyridine-4-carbonitrile in 1.70 ml methanol was treated with under ice cooling with 0.71 ml acetyl chloride (in situ generation of hydrogen chloride), the solution was refluxed for 4 hour, cooled to r.t. and evaporated under reduced pressure, the residue was treated with 1.0 ml MTBE and extracted with 1.0 ml 1M $NaHCO_3$, the separated organic layer was dried with $Na_2SO_4$, filtered and evaporated under reduced pressure to obtain 0.16 g 2-trifluoromethyl-isonicotinic acid methyl ester.
GC-EI-MS: M 205+.

The invention claimed is:
1. A process for the preparation of 2-trifluoromethyl isonicotinic acid and esters of the formula

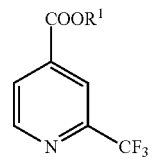

I wherein $R^1$ is hydrogen or $C_{1-6}$-alkyl, comprising the conversion of a 2-trifluoromethyl pyridine derivative of the formula

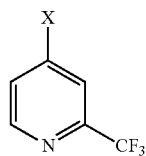

II wherein X is halogen or $-OSO_2CY_3$, wherein Y is halogen, by either palladium-catalyzed: (i) cyanation of II and subsequent hydrolysis of the nitrile to afford I, or, (ii) carbonylation of II in the presence of $R^1OH$ to afford I.

2. The process of claim 1, wherein the conversion comprises the palladium-catalyzed reaction of II with carbon monoxide (CO) in the presence of the reactant $R^1OH$, wherein $R^1$ is hydrogen or $C_{1-6}$-alkyl.

3. The process of claim 1, wherein the conversion comprises the palladium-catalyzed reaction of II with a metal cyanide MCN, wherein M stands for a metal ion to form a nitrile of formula IV

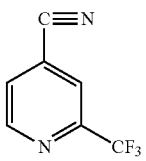

IV and the further hydrolysis or esterification of IV to form the 2-trifluoromethyl isonicotinic acid and esters of the formula I.

4. The process of claim 1, wherein the palladium-complex catalyst is selected from bis(benzonitrile)palladium(II)-chloride, tris(dibenzylideneacetone)dipalladium(0), palladium(II) acetate, or palladium(II)chloride with the ligands selected from 1,1-bis(diphenylphosphino)ethane (dppe), 1,1' bis-(diphenylphosphino)ferrocen (dppf), bis(diphenylphosphino)methane (dppm), 1,3-bis(diphenylphosphino)propane (dppp), 4,5-bis(diphenylphosphino)-9,9-dimethylxanthene or triphenylphosphine.

5. The process of claim 2, wherein the palladium complex catalyst is selected from palladium(II)chloride with the ligands 1,1'-bis(diphenylphosphino)ferrocen (dppf) or 1,3-bis(diphenylphosphino)propane (dppp).

6. The process of claim 2, wherein the conversion is performed under a CO pressure of 5 bar to 100 bar.

7. The process of claim 2, wherein the conversion is performed in the presence of a base.

8. The process of claim 2, wherein the conversion is performed at a reaction temperature between 50° C. and 170° C.

9. The process of claim 2, wherein the conversion to I wherein $R^1$ is $C_{1-6}$ alkyl is carried out in the presence of hydrogen chloride.

10. The process of claim 9, wherein the hydrogen chloride is produced by adding thionyl chloride or acetyl chloride.

11. The process of claim 10, wherein the hydrogen chloride is produced under reflux conditions of the reaction mixture.

12. The process of claim 3, wherein the palladium complex catalyst is selected from Pd(PPh$_3$)$_4$(0), 1,1'-bis(diphenylphosphino)ferrocene-palladium(II)dichloride dichloromethane adduct, Pd(P-tert-Bu$_3$)$_2$, tris(dibenzylideneacetone)dipalladium(0) or Pd(TFA)$_2$ with the ligands 1,1'-bis(diphenylphosphino)ferrocen (dppf) or rac-2-(di-tert-butylphosphino)-1,1-binaphthyl.

13. The process of claim 3, wherein the metal cyanide MCN is zinc cyanide, or zinc cyanide with a mixture with sodium cyanide or potassium cyanide.

14. The process of claim 3, wherein the conversion is performed at a reaction temperature between 50° C. and 120° C.

15. The process of claim 3, wherein the hydrolysis of the nitrile of formula IV to the 2-trifluoromethyl isonicotinic acid of formula I with $R^1$=hydrogen is performed with a base.

16. The process of claim 15, wherein the base is an alkali hydroxide.

17. The process of claim 3, wherein the esterification of the nitrile of formula IV to afford the 2-trifluoromethyl isonicotinic acid ester of formula I with $R^1$=$C_{1-6}$-alkyl is performed with an alcohol $R^1$OH, wherein $R^1$ is $C_{1-6}$-alkyl in the presence of hydrogen chloride.

18. The process of claim 17, wherein the hydrogen chloride is produced by adding thionyl chloride or acetyl chloride.

19. The process of claim 1, wherein $R^1$ is hydrogen, methyl, ethyl or i-propyl.

20. The process of claim 1, wherein $R^1$ is hydrogen or methyl.

21. The process of claim 1, wherein X is fluorine, chlorine, bromine, iodine or trifluoromethanesulfonyl.

22. The process of claim 1, wherein X is chlorine.

\* \* \* \* \*